US00PP21958P3

(12) United States Plant Patent
Brown

(10) Patent No.: US PP21,958 P3
(45) Date of Patent: May 31, 2011

(54) ***LOBELIA* PLANT NAMED 'FRIED GREEN TOMATOES'**

(50) Latin Name: *Lobelia cardinalis*
Varietal Denomination: Fried Green Tomatoes

(75) Inventor: James Dean Brown, Bridgeton, NJ (US)

(73) Assignee: Plants Nouveau a division of Treadwell Palmer International, Inc., Baltimore, MD (US)

( * ) Notice: Subject to any disclaimer, the term of this patent is extended or adjusted under 35 U.S.C. 154(b) by 0 days.

(21) Appl. No.: 12/589,993

(22) Filed: Nov. 2, 2009

(65) Prior Publication Data

US 2011/0107485 P1 May 5, 2011

(51) Int. Cl.
*A01H 5/00* (2006.01)

(52) U.S. Cl. ..... Plt./451

(58) Field of Classification Search ..... Plt./451
See application file for complete search history.

*Primary Examiner* — June Hwu
(74) *Attorney, Agent, or Firm* — Penny J. Aguirre

(57) ABSTRACT

A new and distinct *Lobelia cardinalis* plant characterized by deep purple foliage and tomato red blooms.

2 Drawing Sheets

Botanical denomination: *Lobelia cardinalis.*
Variety denomination: 'Fried Green Tomatoes'.

BACKGROUND OF THE INVENTION

The present invention relates to a new and distinct cultivar of *Lobelia* and given the cultivar name 'Fried Green Tomatoes'. *Lobelia* is in the family Campanulaceae. *Lobelia cardinalis* 'Fried Green Tomatoes' originated as a seedling from a sowing of seeds of the species *Lobelia cardinalis* in a greenhouse at a nursery in Bridgeton, N.J.

Compared to typical plants of the species *Lobelia cardinalis,* the new cultivar has foliage that is purple in color in spring and green with interveinal green in summer rather than green, is more tolerant of average soils, and exhibits a more vigorous growth habit. The new cultivar can be compared to *Lobelia cardinalis* cultivar 'Golden Torch' (U.S. Plant Pat. No. 19,844) which differs from 'Fried Green Tomatoes' in having new foliage growth that is golden in color and in having a less vigorous growth habit. The new cultivar can also be compared to *Lobelia* 'Queen Victoria' (not patented), which differs from 'Fried Green Tomatoes' in being a hybrid of unknown origin that has a less vigorous growth habit, purple foliage that does not last as long in the season, and in having a plant habit that flops in a typical garden.

This new cultivar has been reproduced only by asexual propagation (tip cuttings and divisions). Each of the clones exhibited identical characteristics to the original plant. Asexual propagation by division, standard technique, as done in Bridgeton, N.J., shows that the foregoing characteristics and distinctions come true and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
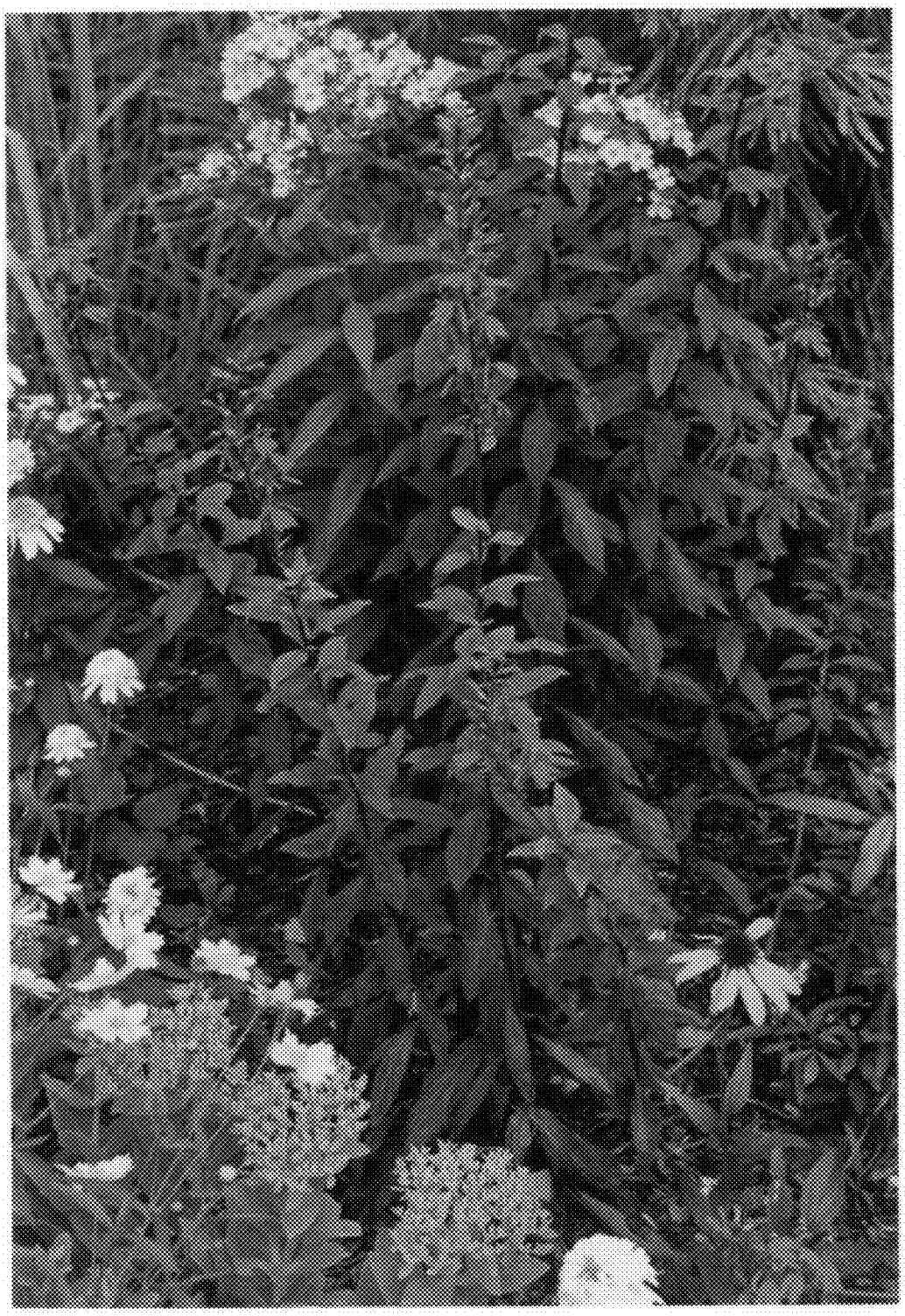
FIG. 1: shows a two year-old plant of *Lobelia* 'Fried Green Tomatoes' growing in the ground in full sun in August in Baltimore, Md.
Figure 2:
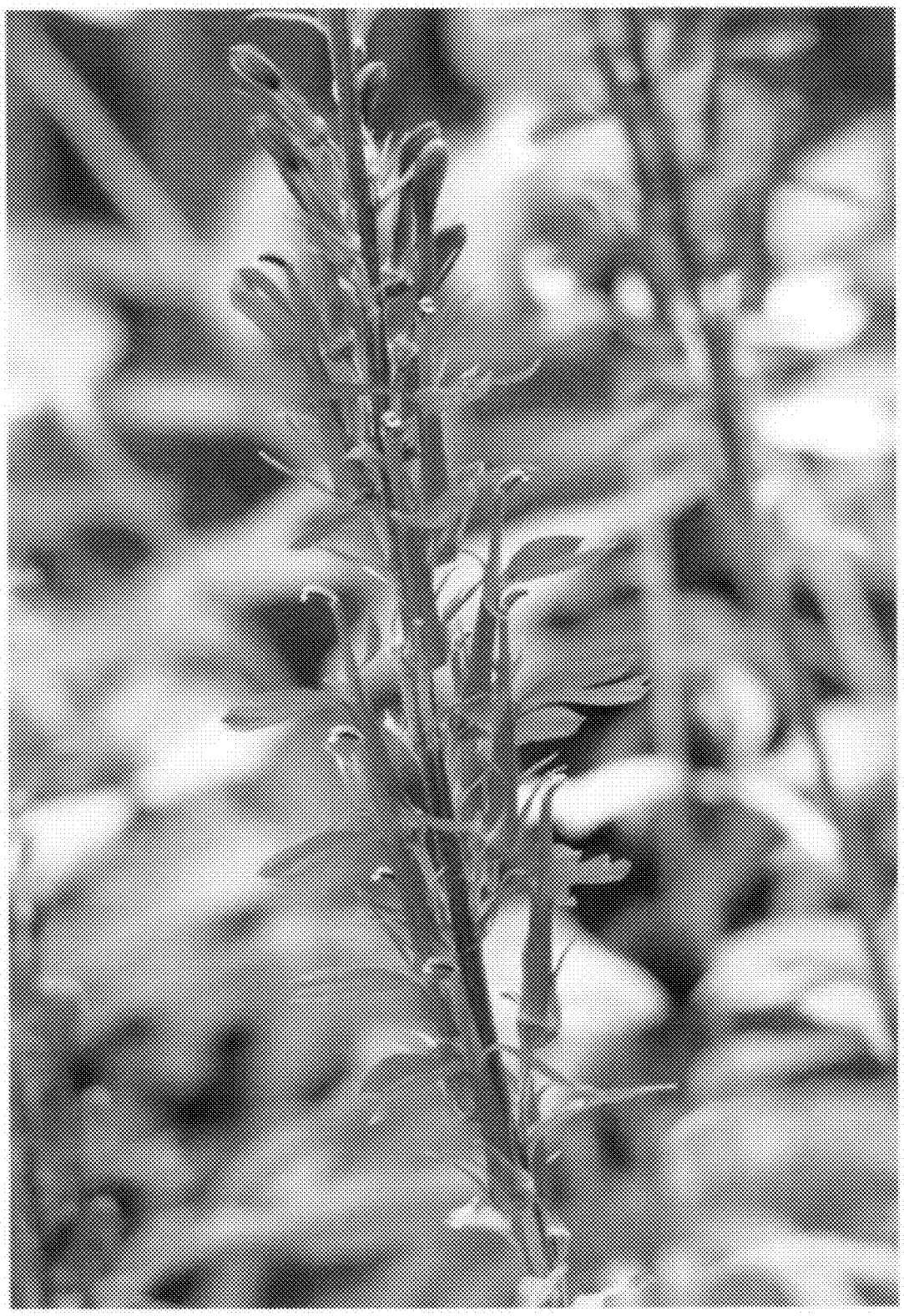
FIG. 2: shows a bloom close-up in August in Baltimore, Md.

The following is a detailed description of the new *Lobelia* cultivar based on observations taken in August of a one year-old specimen growing in the ground in a trial bed in full sun with added irrigation in Baltimore, Md. Baltimore is zone 7 on the USDA Hardiness zone map. Temperatures range from a high of 87 degrees F. in August to an average of 44 degrees F. in January. Normal rainfall in Baltimore is 45 inches per year. The color descriptions are all based on The Royal Horticultural Society Colour Chart.

Plant:
- *Form.*—Herbaceous perennial.
- *Hardiness.*—USDA Zone 3 to 9.
- *Size.*—60 cm to 100 cm tall from top of the flower to the ground and 40 to 50 cm wide.
- *Habit.*—Upright.
- *Vigor.*—Excellent.

Basal leaf:
- *Type.*—Simple.
- *Arrangement.*—Rosulate.
- *Shape.*—Narrowly ovate.
- *Venation.*—Pinnate.
- *Margins.*—Dentate (toothed).
- *Apex.*—Obtuse.
- *Base.*—Cuneate.
- *Blade size.*—7 cm long on average and 2.5 cm wide.
- *Petiole.*—None, sessile.
- *Surface texture.*—Glabrous on both sides.
- *Leaf color.*—Topside, Greyed-Purple N186A with an overlay of Purple group N79B in the spring to Green 137A in the summer; bottom side same with an overlay of Purple N77B.

Cauline leaf:
- *Type.*—Simple.
- *Arrangement.*—Alternate.
- *Shape.*—Oblong lanceolate.
- *Venation.*—Pinnate.

*Margins.*—Toothed.
*Apex.*—Acuminate.
*Base.*—Attenuate.
*Blade size.*—10 cm to 16 cm long and 3 to 3.5 cm wide.
*Surface texture.*—Glabrous on top sides, sparsely pubescent on veins on bottom side.
*Petiole.*—Sessile.
*Leaf color.*—Topside, Grey-Brown 199B with Greyed-purple 184B highlights in the spring to Green 137A with areas of Purple Group N79A interveinally in the summer on the new growth on the upper protion of the stem, bottom side same.
*Stem.*—60 to 100 cm in length (including peduncle) and an average of 5 mm in width, color Greyed-Purple 187A, surface texture glabrous.

Inflorescence:
*Size.*—About 5 cm wide and 24 to 33 cm long.
*Type.*—Bracteate spike.
*Number of flowers per spike.*—25 to 55.
*Number of spikes per flowering season.*—10.
*Peduncle.*—50 to 68 cm tall, 8 mm wide at base, Greyed Green 191B with an overlay of Greyed-purple 187A, internodes 2 cm to 3.5 cm long, sparsely pubescent.
*Pedicel.*—14 mm long, Greyed-Green 194B with an overlay of Greyed-purple 187B, sparsely pubescent.
*Bloom period.*—Beginning the second week of July through middle of August in Baltimore, Md.
*Lastingness.*—Each spike blooms for about 5 weeks.

Flower bud:
*Size.*—5 mm wide and 3 cm long.
*Description.*—Glandular puberulent, tubular.
*Color.*—Greyed — Red 181A.
*Flower type.*—Perfect.
*Shape.*—Bilabiate, lower three lobes spreading, upper 2 lobes recurved.
*Size.*—3.5 cm long and 2 cm wide.
*Corolla description.*—Tube 13 mm long and 5 mm wide, 5 lobes, lower three cut ⅓ to ⅔ of their length, each 10 mm long and 4 mm wide, elliptic, tip acute, margin entire, glabrous on both sides, Red 45B on top side and Red 45D on bottom side with tube portion Red Group 43C on inner surface and Red Group 43A on outer surface.
*Calyx description.*—Campanulate over ovary with 5 long narrow lobes around the corolla, each lobe 14 mm long and 1 mm wide, with 5 lobes, divided ½ way to the base, tip acuminate, margin entire, glabrous on both sides. Yellow-Green 144B outside and Yellow-Green 144B tinted Greyed-Purple 187A on inside lobe tips.
*Stamen description.*—5 in number, overall 33 mm long and 3 mm wide; filaments fused and flattened, encircling style, each filament 26 mm long and about 1 mm wide, Red 45B on top third, Red 37B on middle third lightening to White 155B at the base, anthers fertile, 4 mm long, Greyed-Purple 186B to maturing to Brown 200A; pollen Yellow 12A.
*Pistil description.*—1 in number, 35 mm long; ovary 7 mm long and 5 mm wide, Greyed-Yellow 162B; style 30 mm long, Red 53B, stigma Black 202A surrounded by white hairs.
*Fragrance.*—None.

Fruit:
*Type.*—Ovoid capsule.
*Size.*—1 cm wide.
*Fertility.*—Good.
*Color.*—Brown 200D.

Seed:
*Shape.*—Warty ovoid.
*Size.*—1 mm.
*Color.*—Grey-Brown 199A.

Pest and disease tolerance: No known pest or disease resistances.

I claim:

1. A new and distinct *Lobelia* plant as herein illustrated and described.

* * * * *